US00PP27516P3

(12) United States Plant Patent
Madsen

(10) Patent No.: US PP27,516 P3
(45) Date of Patent: Dec. 27, 2016

(54) *CAMPANULA* PLANT NAMED 'PKM03'

(50) Latin Name: ***Campanula* hybrid**
Varietal Denomination: PKM03

(71) Applicant: Gartneriet PKM A/S, Odense N (DK)

(72) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 122 days.

(21) Appl. No.: 14/544,525

(22) Filed: Jan. 15, 2015

(65) Prior Publication Data

US 2016/0212914 P1 Jul. 21, 2016

(51) Int. Cl.
*A01H 5/00* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from Pluto Plant Variety Database for corresponding Canadian application No. 15-8534 filed Feb. 25, 2015 (1 page) (http://www.wipo.int/pluto).
Printout of application information from Pluto Plant Variety Database for corresponding CPVO application No. 2014/3477 filed Dec. 18, 2014 (1 page) (http://www.wipo.int/pluto).

*Primary Examiner* — Susan McCormick Ewoldt
(74) *Attorney, Agent, or Firm* — Foley & Lardner LLP

(57) ABSTRACT

A distinct cultivar of *Campanula* plant named 'PKM03' characterized by its upright, freely branching growth habit and bicolored (white/violet) broad campanulate flowers.

3 Drawing Sheets

Latin name of genus and species of the plant claimed: *Campanula* hybrid.

Variety denomination: 'PKM03'.

BACKGROUND OF THE INVENTION

The present invention relates to a new and distinct cultivar of *Campanula* plant, botanically known as *Campanula* hybrid, common name Bellflower and hereinafter referred to by the name 'PKM03'.

The new *Campanula* originated from a planned cross between two different *Campanula* species; the female parent being an unnamed, proprietary *Campanula* variety (unpatented) and the male parent being an unnamed, proprietary *Campanula* variety (unpatented). The initial crossing was performed in 2012 by the Inventor, followed by further testing and selection in 2013 after vegetative propagation.

Vegetative propagation was performed by terminal cuttings taken and propagated in Søhus, Denmark. Asexual reproduction of the new *Campanula* cultivar by terminal cuttings has demonstrated that the combination of characteristics as herein disclosed for the new cultivar are firmly fixed and retained through successive generations of asexual reproduction. The new cultivar asexually reproduces true-to-type.

SUMMARY OF THE INVENTION

The following traits have been repeatedly observed and are determined to be the unique characteristics of 'PKM03'. These characteristics in combination distinguish 'PKM03' as a new and distinct cultivar:

1. Upright and freely branching growth habit;
2. Bicolored flowers.

Plants of the cultivar 'PKM03' can be compared to plants of the *Campanula isophylla* cultivar 'Havibi806' (unpatented in the US; registered as CPVO Grant No. 32763). In side-by-side comparisons conducted by the Inventor in Søhus, Denmark, 'PKM03' and 'Havibi806' differ in the following characteristics:

'PKM03' has stiffer and stronger stems than 'Havibi806'.

2. 'PKM03' has a sharper border between the two colors on the flower than 'Havibi806'.

BRIEF DESCRIPTION OF THE PHOTOGRAPHS

The accompanying colored photographs illustrate the overall appearance of the new *Campanula 'PKM*03', showing the colors as true as it is reasonably possible to obtain in colored reproductions of this type. Colors in the photographs may differ slightly from the color values cited in the detailed botanical description, which more accurately describe the actual colors of 'PKM03'.

Figure 1:
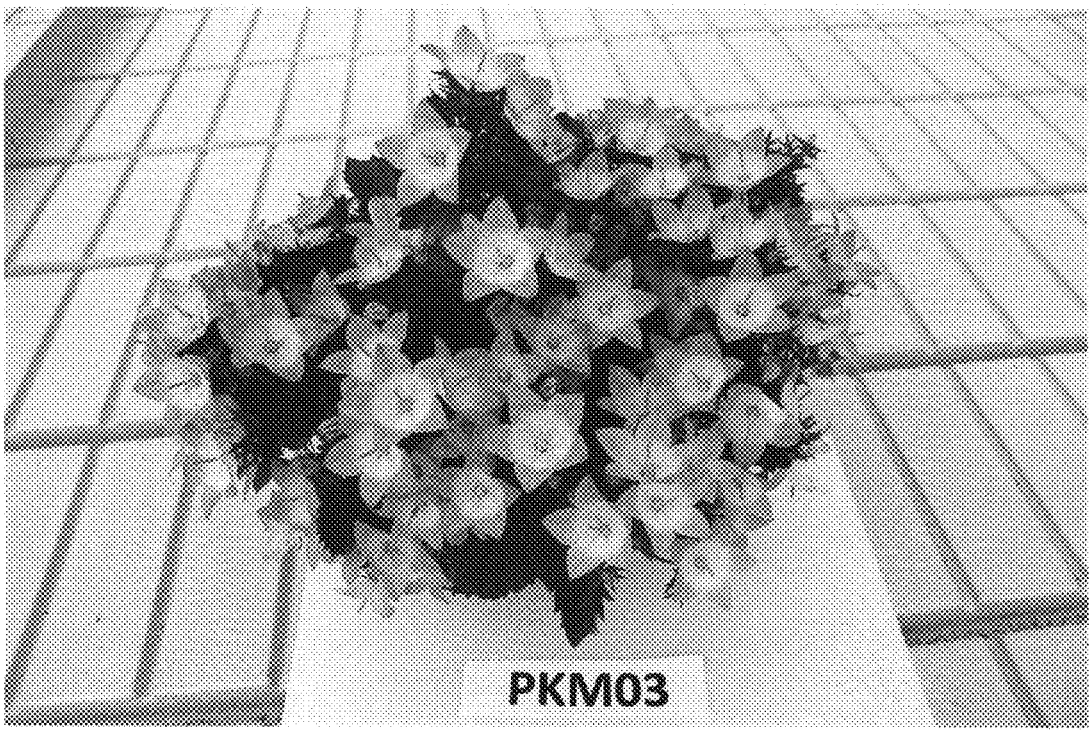

FIG. 1: The photograph comprises a side perspective view of a typical flowering plant of 'PKM03', as grown in a 10.5 cm pot.

Figure 2:
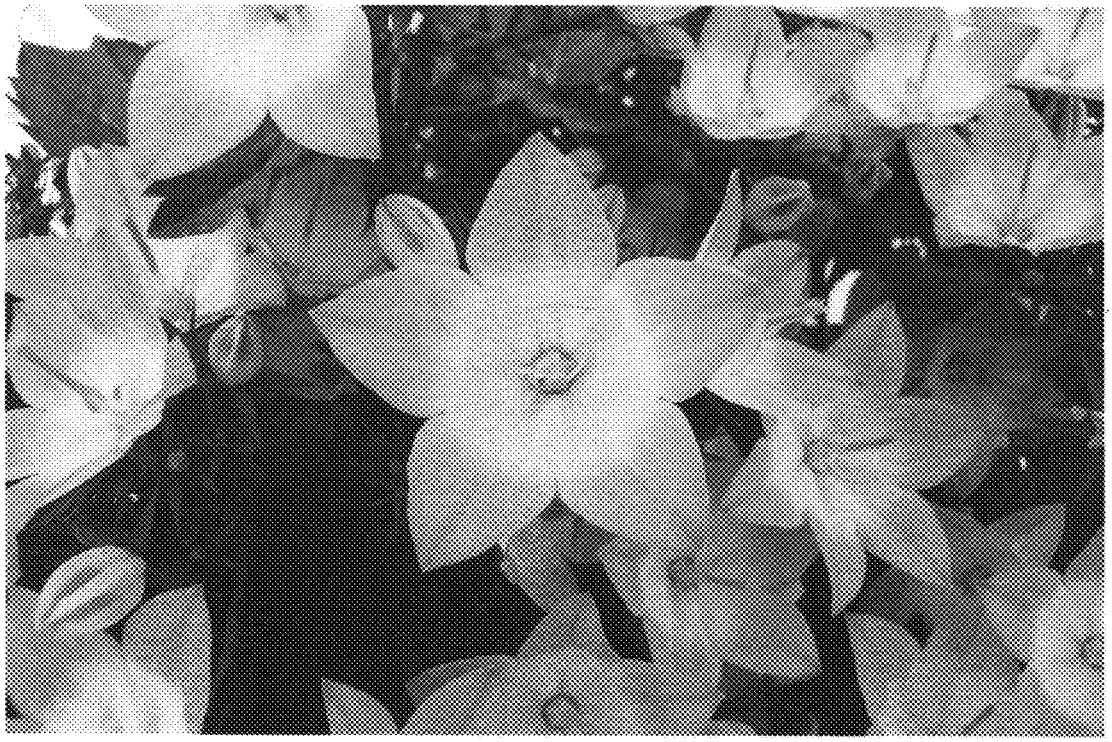

FIG. 2: The photograph comprises a close-up view of a typical inflorescence of 'PKM03'.

Figure 3:
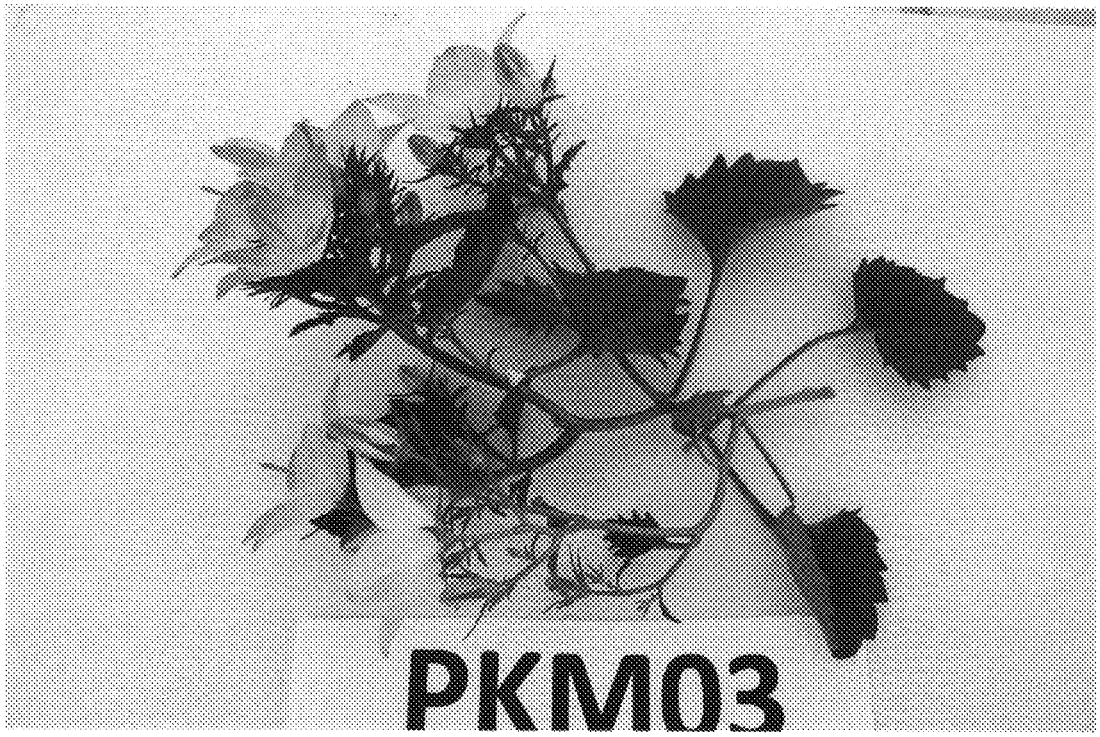

FIG. 3: The photograph comprises a close-up view of a typical lateral branch of 'PKM03', showing typical leaves, buds, and flowers.

DETAILED BOTANICAL DESCRIPTION

The new *Campanula* 'PKM03' has not been observed under all possible environmental conditions. The phenotype of the new cultivar may vary with variations in environment such as temperature, light intensity, day length, growth regulator treatment and fertility level without any variance in genotype.

The aforementioned photographs, together with the following observations, measurements and values describe plants of the new *Campanula* 'PKM03' as grown under greenhouse conditions in an 10.5 cm pot.

The age of the 'PKM03' plants described is about 14 weeks after propagation. Color references are made to The Royal Horticultural Society Colour Chart (R.H.S.), $5^{th}$ edition, except where general colors of ordinary significance are used.

Classification:

*Botanical.*—*Campanula* hybrid.

Parentage:

*Female or seed parent.*—Unnamed proprietary variety of *Campanula* (unpatented).

*Male or pollen parent.*—Unnamed proprietary variety of *Campanula* (unpatented).

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial, rosette plant with upright growth habit and overall globular shape. Freely branching with basal shoots. No pinching required.

*Crop time.*—After rooting, about 14 weeks are required to produce finished flowering plants in up to 11 cm pots.

*Plant height* (*from soil level to top of plant plane*).—About 12-18 cm.

*Plant spread* (*width*).—About 24-28 cm.

*Vigor.*—Good. Average growth rate.

*Lateral branches.*—Number per plant: 25-35. Length: 11-14 cm (including flowers). Diameter: 2-4 mm. Internode length: 5-30 mm.

*Stem.*—Shape: Round-edged. Strength: Stiff. Color: Green, Between RHS 144C and 145A. Pubescence: None. Lactate: a limited quantity of white lactate is produced.

Foliage description:

*Quantity per lateral branch.*—5-12.

*Leaf arrangement.*—Single, alternate.

*Leaf shape.*—Basal: Ovate to Cordate. Apical: Elliptic.

*Leaf tip.*—Acute (Apical and Basal leaves).

*Leaf base.*—Basal: Orbicular to Cordate. Apical: Acute to Obtuse.

*Leaf length.*—Basal: 30-40 mm. Apical: 10-15 mm.

*Leaf width.*—Basal: 40-50 mm. Apical: 10-25 mm.

*Pubescence.*—None.

*Margin.*—Dentate to Serrate, more prominent on basal than apical leaves.

*Color.*—Upper Surface, RHS 147A, Green. Lower Surface, between RHS 147B and 148B, Green.

*Venation.*—Pattern: Pinnipalmate. Color: Upper Surface: A little paler than leaf blade;, green. Lower Surface: same as blade.

*Petiole.*—Length: Basal: 40-60 mm. Apical: 10-20 mm Diameter: 1-2 mm. Color: 147A, green.

Inflorescence description:

*Flower arrangement and shape.*—Broad campanulate flowers. Upright to spreading arrangement. Inflorescences are panicles.

*Flower longevity.*—Longevity of individual flowers is highly dependent on temperature and light conditions; average about 7-11 days. Flowers persistent. Natural flowering season spring to early summer.

*Inflorescence size.*—Length: 10-12 cm.

*Flowers.*—Quantity per inflorescence: 12-16. Length: 15-20 mm. Diameter: 30-40 mm. Arrangement and Shape: Single, sympetalous, campanulate,. Upright to outward aspect.

*Petal color.*—Upper surface: Base: paler/lighter than RHS 92D , White with a purple/violet tone/hue. Apex: Between RHS 91A and 92A, Violet. Lower surface: Base and Apex 92D. Little darker/more intense at the apex than at the base. Color does not fade. Petal number: 5, fused at lower half. Petal Shape: Obtuse lobes. Petal Margin: Entire. Petal Apex: Acute. Petal Length: 15-17 mm lobes. Petal Width: 10-13 mm maximum on lobes. Petal texture: Smooth. Fragrance: None.

*Sepals.*—Arrangement: Free. Appearance: Glabrous. Quantity per flower: 5. Length: 5-10 mm. Width: 2-3 mm. Overall shape: Deltoid. Apex: Acute. Margin: Entire. Color (mature and immature): Upper and lower surfaces: Green, between RHS 147A and RHS 147B. Pedicel: Length: 5-10 mm. Diameter: About 1 mm. Color: Green, Between RHS 144C and 145A.

*Buds.*—Length: Up to 18 mm. Diameter: Up to 8 mm. Shape: Oblong, ridged. Color: Changes from yellow-green, between RHS 154B and RHS150C, to nearly RHS92D at the apex. Coloration of buds starts at the tip.

Reproductive organs:

*Pistil.*—Quantity: 1. Length: 15-20 mm.

*Style.*—Length: 12-18 mm. Color: almost white at base (lower third), near the color of petals (between 91 A and 92A) at the upper two-third.

*Ovary.*—Color: Green, RHS 147AB.

*Stigma.*—Shape: Tripartite. Color: Greyish-green. Stamen: Number: 5, fused until pollen has been shed. Anther: Shape: Fused; curling after shedding. Size: 5 mm. Color: RHS 158A. Pollen: Amount: None to very little.

Seed production: None observed.

High/low temperature tolerance: Plant is not frost tolerant.

Disease resistance and/or susceptibility: Not tested.

I claim:

1. A new and distinct cultivar of *Campanula* hybrid plant named 'PKM03', as illustrated and described herein.

* * * * *